United States Patent [19]

Mazzacca

[11] 3,989,688

[45] Nov. 2, 1976

[54] PROCESS FOR PRODUCING 6-AMINO PENICILLANIC ACID DERIVATIVES

[75] Inventor: Alfred J. Mazzacca, Rutherford, N.J.

[73] Assignee: Biocraft Laboratories, Inc., Elmwood Park, N.J.

[22] Filed: Oct. 21, 1974

[21] Appl. No.: 516,740

[52] U.S. Cl. .......................................... 260/239.1
[51] Int. Cl.$^2$ ..................................... C07D 499/68
[58] Field of Search ................................ 260/239.1

[56] References Cited
OTHER PUBLICATIONS

Weissberger 2nd Ed., Part I "Separation and Purification" (1949).

Primary Examiner—Gerald A. Schwartz
Attorney, Agent, or Firm—Lane, Aitken, Dunner & Ziems

[57] ABSTRACT

A process for producing α-amino and α-amino-substituted-benzylpenicillins in high yield and purity by separately removing solid contaminants from a solution containing a 6-aminopenicillanic acid reactant and an acylating agent solution prior to combining them in a reaction mixture.

4 Claims, No Drawings

PROCESS FOR PRODUCING 6-AMINO PENICILLANIC ACID DERIVATIVES

BACKGROUND OF THE INVENTION

This invention relates to a process for the preparation of amino-substituted penicillins and, more particularly, to an efficient process for producing α-aminobenzylpenicillin and related ring-substituted compounds in high yield and purity.

α-Aminobenzylpenicillin and α-amino-substituted-benzylpenicillins are well known in the art and numerous processes have been proposed for their production. In general these processes involve the reaction of 6-amino-penicillanic acid with an acylating agent such as the acid chloride, acid bromide, acid anhydride, and mixed anhydride of a derivative of α-aminophenylacetic acid or α-amino-substituted-phenylacetic acid in which the amino group is protected with a suitable protecting group.

These known methods for the preparation of α-aminobenzylpenicillins and α-amino-substituted benzylpenicillins by the acylation of 6-aminopenicillanic acid result in the preparation of mixtures which contain, in addition to the desired penicillin, unreacted starting materials, hydrolyzed acylating agent, and products of side reactions which are often difficult to separate from the desired penicillin reaction product.

Various ways have been proposed in the past to remove these unwanted materials such as, for example, the formation of insoluble arylsulfonic acid salts of α-aminobenzylpenicillin as described in U.S. Pat. No. 3,180,862, or the even more complex isolation process of U.S. Pat. No. 3,271,389, but in each case the known recovery procedures have been concentrated on removing the contaminants after the desired α-amino-substituted benzyl penicillins have been formed. Consequently, these known processes are characterized by complex procedures which at the very least increase the cost of producing the desired penicillin product.

SUMMARY OF THE INVENTION

It has now been discovered that α-aminobenzylpenicillin and α-amino-substituted-benzylpenicillins may be produced in high yield and purity by separately removing unwanted solid contaminants from a solution of aminopenicillanic acid (preferably in the form of a water-soluble salt) and removing unwanted solid contaminants from a solution of an acylating agent, preferably by filtration, before combining them in a reaction mixture. Because of the known instability of mixed anhydrides when used as acylating agents, a relatively low temperature, i.e., about −50° C, will preferably be maintained following its formation and its separation from unwanted contaminants prior to its mixture with the solution containing 6-aminopenicillanic acid or its water-soluble salt.

Accordingly, it is a principal object of the present invention to provide an efficient process for producing α-aminobenzylpenicillin and α-amino-substituted-benzylpenicillins in high yield and purity. This and other objects of the present invention are achieved in the manner briefly summarized above and described in greater detail in the ensuing discussion.

DESCRIPTION OF THE PREFERRED EMBODIMENTS

The compounds produced according to the process of this invention include those having the general formula:

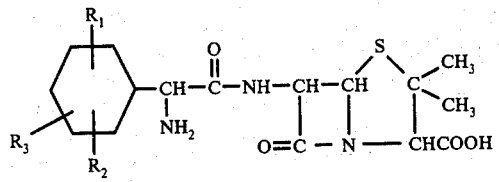

wherein $R^1$, $R^2$ and $R^3$ each represents a member selected from the group consisting of hydrogen, nitro, di(lower)alkylamino, (lower)alkanoylamino, (lower)alkanoyloxy, (lower)alkyl (including straight and branched chain saturated aliphatic groups having from 1 to 6 carbon atoms inclusive), (lower)alkoxy, hydroxy, sulfamyl, chloro, iodo, bromo, fluoro, trifluoromethyl, (lower)alkylthio, (lower) alkyl-sulfonyl, carbo(lower)alkoxy, benzyl, phenethyl, cycloheptyl, cyclohexyl and cyclopentyl; and their sodium, potassium, calcium, aluminum and ammonium salts with an amine selected from the group consisting of trialkylamines, procaine, dibenzylamine, N-benzylbeta-phenethylamine, 1-ephenamide, N,N'-dibenzylethylenediamine, dehydroabietylamine, N,N'-bis-dehydroabietylethylenediamine, N-(lower) alkylpiperidine, and other amines which have been used to form salts of benzylpenicillin, as well as easily hydrolyzed esters or amides which may be converted to the free form by chemical or enzymatic hydrolysis and the anhydrous and hydrated forms of these compounds. Also, recognizing the fact that the above compounds can exist in two optically active isomeric forms, i.e., the D- and L-diastereoisomers, as well as a racemic mixture of such forms, it should be understood that the process of this invention extends to the preparation of such isomeric forms of the compounds.

The products of the present invention may be prepared by reacting 6-aminopenicillanic acid, preferably in the form of a water-soluble salt such as the sodium salt or triethylamine salt, with an acylating agent such as a carboxylic acid chloride or bromide, an ester of chlorocarbonic acid, an acid azide, an acid anhydride of a carboxylic acid, or preferably, a mixed acid anhydride derived from a carboxylic acid.

The 6-aminopenicillanic acid or water-soluble salt thereof utilized in this invention may be produced by any of the known methods such as, for example, the procedure disclosed in U.S. Pat. No. 3,499,909.

The acylating agent may also be prepared by known procedures, an example of which may be found in U.S. Pat. Nos. 3,576,797 and 3,071,575. In a preferred embodiment the acylating agent will be a mixed anhydride prepared, for example, by reacting an N-protected amino-substituted carboxylic acid salt (such as described by Dane et. al., *Angew Chem.*, 1962, 74,873. with an ester of chlorocarbonic acid, e.g., ethylchlorocarbonate.

Because of the known instability of mixed anhydrides, it is particularly useful in this embodiment to maintain the mixed anhydride in an anhydrous, inert and preferably water-miscible solvent, such as p-dioxane or acetone, which is kept at a temperature of about −50° C or below.

Whichever method is employed in producing the 6-aminopenicillanic acid and acylating agent according to this invention, before bringing them together in solution in a reaction mixture the reactants are separately treated to remove contaminants such as unreacted starting materials or impurities therein, reaction by-products, and the like, therefrom. Any conventional method may be used for this purpose although filtration is the most convenient and, therefore, the preferred procedure.

After the reactants are treated to remove the contaminants, they are mixed together according to known procedures to produce the α-amino- or α-amino-substituted-benzylpenicillins.

The following example will further illustrate the invention.

EXAMPLE

A mixed anhydride solution of 96 kg. of N-(2-carbethoxy-1-methylvinyl)-2- phenylglycine ethoxyformic anhydride in 785 liters of acetone was filtered to remove solid material therefrom and maintained at a temperature of about −50° C. In a separate mixing container, 60 kg. of 6-aminopenicillanic acid in 100 liters of water was mixed with 39 liters of triethylamine while maintaining the temperature between 5°–15° C and a pH of between 8.0–8.7. The resulting triethylammonium salt of 6-aminopenicillanic acid in solution was filtered, maintained at a temperature of about −20° C and rapidly added to the mixed anhydride solution where mixing was continued for about 1 hour while maintaining a reactor temperature below −42° C. The reaction mixture was diluted with water, brought to pH 1.5 with hydrochloric acid, and agitated at 0° C for ½ hour. It was then twice extracted with methylene chloride, the water phases being retained, and treated with ammonium hydroxide to precipitate a solid which was collected, washed with water, dried, and identified as D-(−)-α-aminobenzylpenicillin trihydrate.

When the term α-aminobenzylpenicillin is used in the ensuing claims it is intended to encompass α-amino-substituted-benzylpenicillins and all of the derivatives hereinbefore described.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A process for the production of an α-aminobenzylpenicillin comprising forming a solution of 6-aminopenicillanic acid or its water-soluble salt, removing solid contaminants from the 6-aminopenicillanic acid solution, separately forming a mixed anhydride acylating agent in solution, cooling said acylating agent solution to maintain a temperature of about −50° C or below, removing solid contaminants from the cooled acylating agent solution, combining said 6-aminopenicillanic acid solution and said acylating agent solution in a reaction mixture to produce the desired α-aminobenzylpenicillin, and recovering the α-aminobenzylpenicillin.

2. A process according to claim 1 wherein said solid contaminants are removed by filtration.

3. A process for the production of an α-aminobenzylpenicillin comprising forming an aqueous solution of the triethylammonium salt of 6-aminopenicillanic acid, removing solid contaminants from the salt solution, separately forming a water-miscible organic solvent solution of a mixed anhydride acylating agent, cooling said acylating agent solution to maintain a temperature of about −50° C or below, removing solid contaminants from the cooled acylating agent solution, combining said 6-aminopenicillanic acid salt solution and said acylating agent solution in a reaction mixture to produce the desired α-aminobenzylpenicillin, and recovering the α-aminobenzylpenicillin.

4. A process according to claim 3 wherein the reaction product is D-(−)-α-aminobenzylpenicillin.

* * * * *